US 11,493,509 B2

(12) United States Patent
Hatamian

(10) Patent No.: US 11,493,509 B2
(45) Date of Patent: Nov. 8, 2022

(54) LATERAL FLOW ASSAY FOR DETECTING MULTIPLE PROTEINS OF A PATHOGEN

(71) Applicant: 2Pi-Sigma Corp., Newport Beach, CA (US)

(72) Inventor: Mehdi Hatamian, Mission Viejo, CA (US)

(73) Assignee: 2Pi-Sigma Corp., Newport Beach, CA (US)

( * ) Notice: Subject to any disclaimer, the term of this patent is extended or adjusted under 35 U.S.C. 154(b) by 0 days.

(21) Appl. No.: 17/232,553

(22) Filed: Apr. 16, 2021

(65) Prior Publication Data

US 2021/0325383 A1 Oct. 21, 2021

Related U.S. Application Data

(60) Provisional application No. 63/011,282, filed on Apr. 16, 2020.

(51) Int. Cl.
*G01N 33/543* (2006.01)

(52) U.S. Cl.
CPC ... *G01N 33/54386* (2013.01); *G01N 2469/20* (2013.01)

(58) Field of Classification Search
CPC .......... G01N 33/54386; G01N 2469/20
See application file for complete search history.

(56) References Cited

U.S. PATENT DOCUMENTS

| 7,318,436 | B2* | 1/2008 | Snow | A61M 15/0045 |
| | | | | 128/203.21 |
| 10,887,104 | B1* | 1/2021 | Jayachandran | H04L 9/3239 |
| 2013/0280696 | A1* | 10/2013 | Millenson | G01N 33/54366 |
| | | | | 435/5 |
| 2016/0370366 | A1* | 12/2016 | Fleming | B01L 9/527 |

OTHER PUBLICATIONS

"Recent Developments in Covid-19 Diagnostic Testing" Mar. 19, 2020, Rachel Muenz, p. 1-17 (Year: 2020).*
"Tell Me Fast Novel Coronavirus (Covid-19) IgG/IgM Antibody Test Intended Use" Aug. 2020 Biocan Diagnostics pp. 1-8 (Year: 2020).*
"Cellex qSARS-CoV-2 IgG/IgM Cassette Rapid Test", FDA Intended Use. Available online on or before Apr. 12, 2020 as evidenced by wayback machine. pp. 1-4, (Year: 2020).*

(Continued)

*Primary Examiner* — Dennis White
(74) *Attorney, Agent, or Firm* — Makoui Law, PC; Ali Makoui

(57) ABSTRACT

A lateral flow assay device includes a test strip that is configured to receive a sample fluid and detect a presence of antibodies to one or more of a plurality of proteins of the target pathogen. The lateral flow assay device includes a conjugate pad and a membrane. The conjugate pad contains a plurality of the proteins of the target pathogen, each conjugated with a label. If the sample fluid contains antibodies that are specific to the target pathogen through any of the target pathogen's proteins, a binding takes place between those antibodies and the corresponding tagged protein. The membrane may include a plurality of test lines. Each test line may contain the immobilized binding reagent to one antibody class, resulting in the concentration of all the molecules of that antibody class on the test line.

20 Claims, 8 Drawing Sheets

(56) References Cited

OTHER PUBLICATIONS

Erasmus MC, "Clinical sensitivity and specificity of three rapid SARS-CoV-2 Antibody (IgM/IgG) Tests on a hospitalized patient cohort: InTec, Cellex and OrientGene" Apr. 8, 2020, (Year: 2020).*

"qSARS-CoV-2 IgG/IgM Cassette Rapid Test (GICA)", FDA Intended Use. Available online May 12, 2020 as evidenced by wayback machine. pp. 1-4 (Year: 2020).*

Thompson, James, "2019-nCoV Antibodies from ProSci," Caltag Medsystems Life Science Solutions, Mar. 31, 2020.

Author unknown, "Cellex qSARS-CoV-2 IgG/IgM Rapid Test," Cellex, Inc., Available online on Apr. 12, 2020, as evidenced by wayback machine, pp. 1-4.

Author unknown, "Cellex qSARS-CoV-2 IgG/IgM Rapid Test," Cellex, Inc., Available online on May 5, 2020, as evidenced by wayback machine, pp. 1-4.

\* cited by examiner

LATERAL FLOW ASSAY FOR DETECTING MULTIPLE PROTEINS OF A PATHOGEN

CLAIM OF BENEFIT TO PRIOR APPLICATIONS

This application claims the benefit of U.S. Provisional Patent Application Ser. No. 63/011,282, filed on Apr. 16, 2020. The contents of U.S. Provisional Patent Application 63/011,282 are hereby incorporated by reference.

BACKGROUND

Lateral flow assays (LFAs), also referred to as lateral flow immunochromatographic assay or lateral flow dipstick immunoassay, are devices that are used to detect the presence (or absence) of a target analyte in a sample fluid without the need for specialized equipment. The lateral flow assays are widely used for medical diagnostics for point of care testing, home testing, or laboratory use.

A lateral flow assay typically includes a series of capillary pads for transporting fluid. A sandwich assay format may be used for detecting analytes that have at least two binding sites to bind to an antibody. A sample pad is used to receive a quantity of fluid (referred to as the sample fluid) and transport the sample fluid to an adjacent conjugate pad. The conjugate pad contains a solubilized antibody labeled with a detector such as colloidal gold nanoparticles. The antibody is specific to a certain analyte which is the target of interest in the sample fluid. As the sample fluid flows through the conjugate pad, the analyte (if any) in the sample fluid binds with the labeled antibody on the conjugate pad and forms an immunocomplex.

The immunocomplex then flows from the conjugate pad into an adjacent membrane (or membrane pad). The membrane has a test area, or test line, that contains an immobilized unlabeled antibody. As the immunocomplex moves over the test area, the immunocomplex binds with the immobilized antibody on the test area, resulting in a colored test line. When the sample fluid does not include the target analyte, no immunocomplex is formed on the conjugate pad and no immunocomplex binds with the immobilized antibody on the test area. As a result, the test line does not change color.

A lateral flow assay may also include a control line in the membrane. In a sandwich assay format, the control line may contain an immobilized antibody that binds to the free antibodies labeled with the detector resulting in a colored control line, which confirms that the test has operated correctly regardless of whether or not the target analyte has been present in the sample.

A competitive assay format may be used for detecting analytes that cannot simultaneously bind to two antibodies. The sample pad and the conjugate pad in a competitive assay format are similar to the sample pad and the conjugate pad in the sandwich assay format. In the competitive assay format, the test line contains immobilized analyte molecules.

If the sample liquid does not contain the analyte, the labeled antibody flows from the conjugate pad into the test line and binds to the analyte at the test line, resulting in a colored test line that indicates the lack of the target analyte in the sample liquid. If, on the other hand, the target analyte is present in the sample liquid, the analyte binds to the labeled antibodies on the conjugate pad and prevents the labeled antibody to bind to the analyte at the test line, resulting in the lack of color on the test line. In a competitive assay format, the control line may contain an immobilized analyte that binds to the free antibodies labeled with the detector resulting in a colored control line, which confirms that the test has operated correctly regardless of whether or not the target analyte has been present in the sample.

BRIEF DESCRIPTION OF THE DRAWINGS

The various embodiments of the present lateral flow assay for detecting multiple proteins of a virus now will be discussed in detail with an emphasis on highlighting the advantageous features. These embodiments depict the novel and non-obvious lateral flow assay for detecting multiple proteins of a virus shown in the accompanying drawings, which are for illustrative purposes only. These drawings include the following figures, in which like numerals indicate like parts.

DETAILED DESCRIPTION

Figure 1:
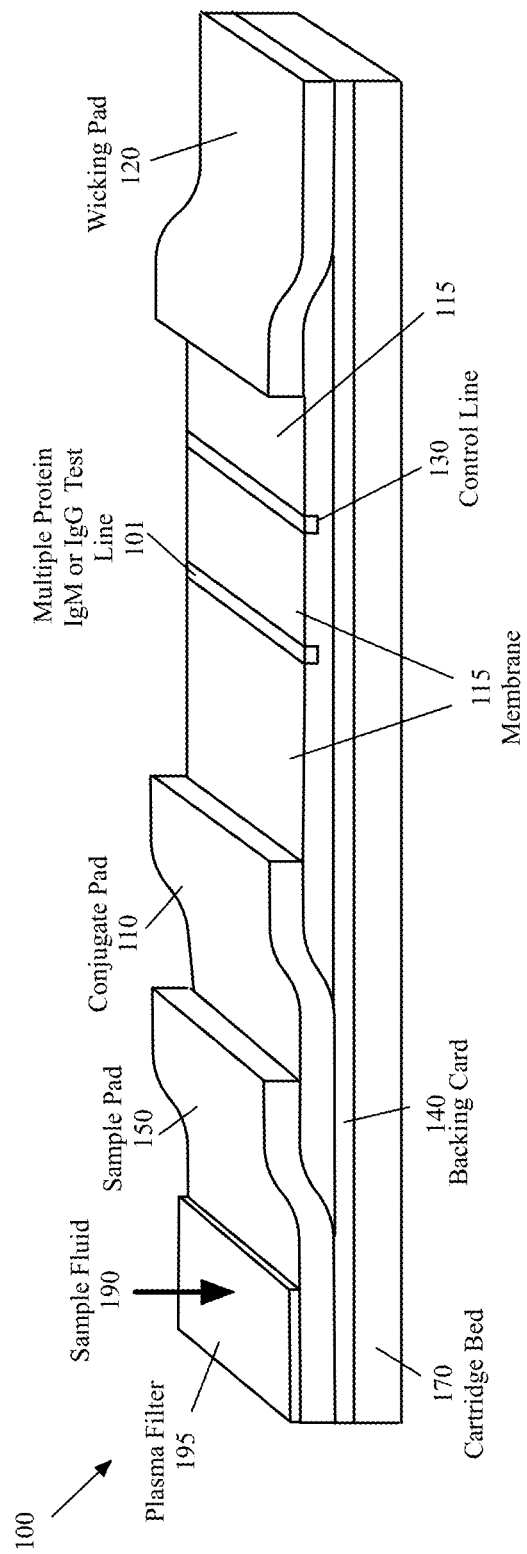
FIG. 1 is an upper front perspective view of an example of a portion of an LFA device, where the conjugate pad contains the antibody to IgM or IgG conjugated with a tag and the test line, in a sandwich format, contains a combination of all or some of the different proteins of the virus, according to various embodiments of the present disclosure.

One aspect of the present embodiments includes the realization that the existing LFA devices that are used to determine whether a subject has been exposed to a pathogen, such as a virus or a bacteria, generate false negatives. These LFA devices may include a conjugate pad that contains a particular protein (or an antigen) of a target pathogen, conjugated with a tag. The LFA devices may include one or more test lines that immobilize the antibody to one or more Immunoglobulins.

If a sample contains any immunoglobulins that are specific to the particular protein of the pathogen, the immunoglobulins may bind to the conjugated protein on the conjugate pad. The resulting immunocomplex may then flow on the membrane of the LFA device where the immunocomplex may bind with the immobilized antibodies of the immunoglobulins on the test line(s). Since the antibody detection tests provided by the currently marketed LFA devices detect only one particular protein of a pathogen, the LFA devices generally show a very high specificity (i.e., there are very small number or even zero false positives) but the false negatives are high due to the low sensitivity of these LFA devices. For example, when the sample does not include the particular protein of the pathogen but includes another protein of the pathogen (which is not included on the conjugate pad), the subject's exposure to the pathogen remains undetected, resulting a false negative.

Some of the present embodiments solve the aforementioned problems by configuring the conjugate pad of an LFA device to contain tagged binding reagents to several immunoglobulins. In order to increase the sensitivity of the test, a combination of all or a plurality (e.g., two or more) of the proteins of a particular target pathogen may be combined and immobilized on the test line forming an aggregate of proteins that can capture any of the Immunoglobulins (e.g., IgM or IgG) responses regardless of which protein of the target pathogen the response has been generated for. The test line in this case may change color if any of those responses are present eliminating the possibility of missing an immune response to the pathogen and reducing the false negatives. Some embodiments may include more than one test line, where each test line is configured to immobilize one or more proteins from the different proteins of the target pathogen.

In some embodiments, the conjugate pad may be configured to contain either all or some (i.e., a plurality of two or more) of the proteins of the target pathogen, each conjugated with a label. If the sample contains antibodies that are specific to the target pathogen through any of the target pathogen's proteins, a binding may take place between those antibodies and the corresponding tagged proteins of the target pathogen. The membrane may include a plurality of test lines. Each test line may contain the immobilized binding reagent to one antibody class, resulting in the concentration of all molecules of that antibody class (e.g., a mix of the molecules of that antibody class against any of the target pathogen's proteins generated by the immune system).

Some embodiments may include a test cartridge that include two test strips. the first test strip may function as any of the LFA devices of the present embodiment that are used to detect the presence of antibodies to a pathogen. The second test strip may be used to receive a saliva sample and detect the presence of the pathogen itself. The second test strip may include a conjugate pad that contains the binding reagent to one of the proteins of the target pathogen. After a binding step on the conjugate pad, the sample fluid may flow over the membrane of the second test strip. The membrane of the second test strip may include a test line, which may contain the binding reagent to a different protein of the target pathogen or a binding reagent to the same protein different from the binding reagent used on the conjugate pad. If the sample contains the pathogen, the pathogens bind with the conjugated binding reagents to the first protein, flow towards the test line, and are stopped at the test line by binding to the binding reagent against another one of the pathogen's protein or against a binding reagent to the same protein different from the binding reagent used on the conjugate pad. The concentration of the pathogen, and hence the tag, may result in a color change of the test line.

The remaining detailed description describes the present embodiments with reference to the drawings. In the drawings, reference numbers label elements of the present embodiments. These reference numbers are reproduced below in connection with the discussion of the corresponding drawing features.

I. LFA Device for Testing the IgM and IgG Response to Presence of Multiple Virus Proteins of a Target Pathogen The immune system makes antibodies or immunoglobulins to fight against antigens. Antigens are molecules or molecule structures that may be present on the outside of a pathogen, such as, bacterium, virus, protozoan, prion, viroid, fungus, etc. The immunoglobulins or antibodies may belong to one of five general classes known as Immunoglobulin M (IgM), Immunoglobulin G (IgG), Immunoglobulin A (IgA), Immunoglobulin D (IgD), and Immunoglobulin E (IgE). Of these classes of immunoglobulins, IgM and IgG play a major role in fighting against bacterial and viral infections. IgM is the first and the early (e.g., within the first few days of exposure to a virus) antibody that is made by the immune system to fight a new infection or a foreign particle invasion. This is followed by the generation of IgG antibodies (e.g., within the first two weeks of exposure) by the immune system against the particular foreign entity it is fighting. IgM provides the immediate response to a foreign entity or a virus that enters the body and its production will generally stop after a short period while IgG provides a later response that has a lasting effect and can help developing secondary immune response against a particular foreign antigen.

Some embodiments of the present invention offer a solution to improve the sensitivity of the test and reduce false negatives. Once a pathogen, such as, for example, and without limitations, a virus enters the body, the immunoglobulins response by the immune system may be made against one or a number of the proteins for that virus. Different individuals may respond differently and may produce different immunoglobulins responses against different proteins of the virus. In the following descriptions, IgM and/or IgG are used as two example immunoglobulins. It should be noted that any one or more of the immunoglobulins IgA, IgD, IgE, IgG, and/or IgM may be used interchangeably.

FIG. 1 is an upper front perspective view of an example of a portion of an LFA device 100, where the conjugate pad 110 contains the antibody to IgM or IgG conjugated with a tag and the test line, in a sandwich format, contains a combination of all or some of the different proteins of the virus, according to various embodiments of the present disclosure.

With reference to FIG. 1, the LFA device 100 may be configured to detect the presence of antibodies to a particular pathogen. While the IgM and IgG antibodies belong to the general class M and G of immunoglobulins, but they are also specific to a protein on the particular pathogen or foreign entity they are meant to attack. As described below with reference to FIG. 2B, antibodies attach to the specific protein on the target pathogen.

Figure 2A:
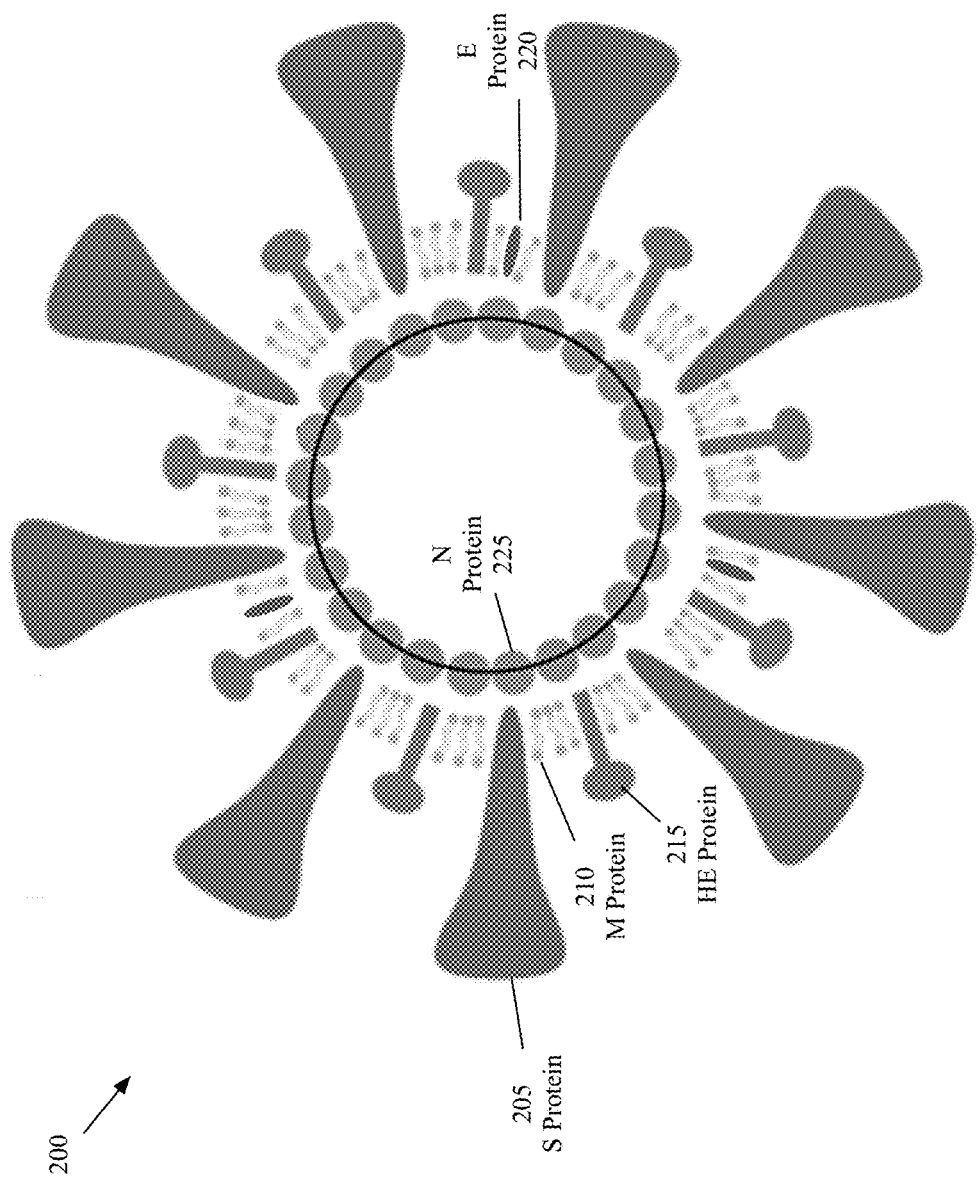
FIG. 2A illustrates the structure and components of a severe acute respiratory syndrome coronavirus 2 (SARS-CoV-2) virus that is responsible for coronavirus disease 2019 (COVID-19) and its major proteins, according to prior art.

As an example, FIG. 2A shows the structure and components of a severe acute respiratory syndrome coronavirus 2 (SARS-CoV-2) virus 200 that is responsible for coronavirus disease 2019 (COVID-19) and its major proteins, according to prior art. FIG. 2A and the following description of the SARS-CoV-2 proteins by ProSci Inc. may be found on the Internet.

The Spike protein (S) 205 is heavily glycosylated, utilizes an N-terminal signal sequence to gain access to the endoplasmic reticulum (ER) and mediate attachment to host receptors. The Spike protein 205 is the largest structure and makes the distinct spikes on the surface of the virus. For most coronaviruses, the Spike protein 205 is cleaved by a host cell furin-like protease into two separate polypeptides S1 and S2.

The Nucleocapsid protein (N) 225 binds to RNA in vitro and is heavily phosphorylated. N proteins bind the viral genome in a beads on a string type conformation. This protein likely helps tether the viral genome to replicase-transcriptase complex (RTC), and subsequently package the encapsulated genome into viral particles.

The Envelope protein (E) 220 is found in small quantities within the virus. The Envelope protein 220 is most likely a transmembrane protein and with ion channel activity. The Envelope protein 220 facilitates assembly and release of the virus and has other functions such as ion channel activity. This protein is not necessary for viral replication but it is for pathogenesis.

The Membrane protein (M) 210 is the most abundant structural protein. The Membrane protein 210 does not contain signal sequence and exists as a dimer in the virion. This protein may have two different conformations to enable it to promote membrane curvature as well as bind to nucleocapsid.

The Hemagglutinin-esterase dimer protein (HE) 215 is present in a subset of betacoronaviruses. The Hemagglutinin-esterase dimer protein 215 binds sialic acids on surface glycoproteins. This protein's activities are thought to enhance S protein-mediated cell entry and virus spread through the mucosa.

Measuring the presence and/or concentration of IgM and IgG antibodies for a given antigen in blood or other bodily fluids is of great importance in both detecting whether an individual has been exposed to a virus as well as obtaining information about the stage of a viral infection. Of particular interest are rapid test kits based on LFA format for either qualitative or quantitative measurement of IgM and IgG that are specific to a particular antigen.

In the SARS-CoV2 example above, some individuals may generate an immune response to the N protein 225 of the SARS-CoV2 virus 200 while others may generate responses to say both the N protein 225 and the S protein 205 or just the S protein 205 or maybe any number of the five proteins 205-225 of the virus 200, each at a different level. A positive patient who has not generated an immune response to the N protein 225 may be characterized as negative by the current tests similar to the example prior art LFA device 500 and 600, described below with reference to FIGS. 5 and 6, respectively. The prior art LFA devices may produce a false negative contributing to the low sensitivity of the test.

In some of the present embodiments, to increase the sensitivity of the test, a combination of all or a plurality (e.g., two or more) of the proteins of a particular target pathogen may be combined and immobilized on the test line forming an aggregate of proteins that can capture any of the IgM or IgG responses regardless of which protein of the target pathogen the response has been generated for. The test line in this case may change color if any of those responses are present eliminating the possibility of missing an immune response to the virus and reducing the false negatives.

Figure 2B:
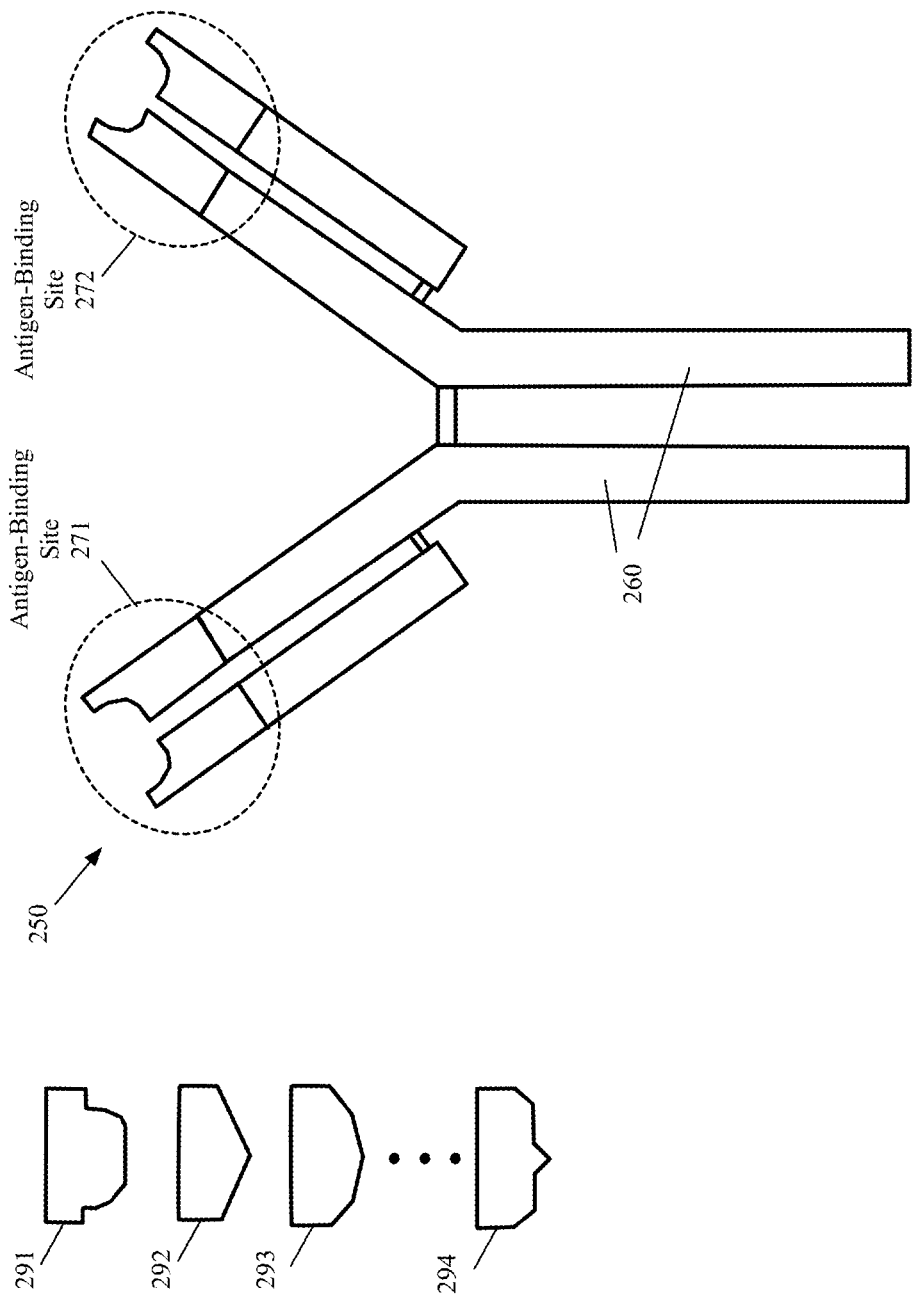
FIG. 2B illustrates an example of antibody with an antigen-binding site to bind to a specific antigen, according to prior art.

FIG. 2B illustrates an example of an antibody with an antigen-binding site to bind to a specific antigen, according to prior art. With reference to FIG. 2B, the antibody (or immunoglobulin) 250 may be a Y-shaped protein used by the immune system to identify and neutralize pathogens. The tips of the Y-shaped protein contain a binding site 271 and 272 that may be specific for a particular antigen, allowing the antigen-binding site 271 or 272 to bind to the specific antigen. The antibody may then either directly neutralize the antigen or may tag the antigen to allow the other parts of the immune system to neutralize the antigen.

To allow the immune system to recognize numerous different antigens 291-294, the antigen-binding sites 271-272 at both tips of the antibodies come in numerous different varieties. For example, there may be an antibody with a specific antigen binding site for each of the proteins 205-225 of the SARS-CoV2 virus 200 of FIG. 2A. The remainder of the antibody 250 may only occurs in a few variants, which define the antibody's above-mentioned classes: IgA, IgD, IgE, IgG, or IgM.

By way of the non-limiting example of the SARS-CoV2 virus 200 (FIG. 2A), the conjugate pad 110 of the LFA 100 (FIG. 1) of the present embodiments may include the binding reagents to IgM and/or IgG, conjugated with a tag. The test line 101 may contain a combination of all or a plurality (e.g., two or more) of the different proteins 205-225 of the SARS-CoV2 virus 200.

The LFA device 100 may be a portable device (e.g., a handheld device or benchtop device) that is used to analyze a sample fluid 190 (also referred to as matrix) to determine the presence and/or the amount of one or more analytes (referred to as target analytes). In this specification, the terms LFA device and LFA are interchangeably used to refer to a device that performs lateral flow tests.

The sample may be human or animal bodily fluid, such as, for example, and without limitations, one or more of blood, serum, plasma, saliva, etc. The sample may naturally be a liquid, may be a liquid diluted with another liquid, such as water, or may have originally been in a solid form (e.g., a tissue sample) and is treated to be in liquid form for the application to the LFA device 100. The target analytes may be substances such as, for example, and without limitations, proteins, haptens, enzymes, hormones, infectious disease agents, immunoglobulins, polynucleotides, steroids, drugs, nucleic acids, markers for gene mutations, etc.

With reference to FIG. 1, the LFA device 100 may include a sample pad 150, a conjugate pad 110, a membrane 115, and optionally a 120. The sample pad 150, the conjugate pad 110, the membrane 115, and the 120 may be made of materials that make a fluid sample applied to the sample pad 150 flow by capillary action downstream (i.e., from the sample pad 150 towards the 120).

The sample pad (also referred to as sample strip or sample receiving member) 150 may be made of natural and/or synthetic porous, microporous, mesoporous, or macroporous materials capable of receiving a sample fluid and laterally conducting the sample fluid towards the sample pad 150 by capillary action. The sample pad 150 may be made of a material such as, for example, and without limitations, cellulose, nitrocellulose, paper, silica, cotton, glass (e.g., glass fiber), or synthetic material (e.g., polyester, polyethylene, polymers, rayon, nylon, etc.). Depending on the type of the sample (e.g., urine, saliva, blood, etc.), the sample pad 150 may be treated by a buffer (e.g., an organic compound such as tris or tris(hydroxymethyl)aminomethane) to mitigate sample variabilities (pH, protein concentration, viscosity, salt concentration, etc.). During the manufacture of the sample pad 150, the buffer compound may be coated, impregnated, or otherwise applied or deposited on the sample pad 150 and then dried.

With further reference to FIG. 1, the conjugate pad 110 is fluidically connected (i.e., capable of receiving fluid, e.g., by capillary action) to the sample pad 150. In the depicted embodiment, the sample pad 150 is in contact with and partially covers the conjugate pad 110. In other embodiments, the sample pad 150 may be in more contact or less contact with the conjugate pad 110 in order to provide slower or faster binding reagent and/or conjugate release respectively. A sample fluid that may be applied to the sample pad 150 (e.g., through a plasma filter 195 when the sample fluid is blood). The sample fluid may be laterally transferred from the sample pad 150 to the conjugate pad 110 by capillary action.

The conjugate pad 110 may be made of natural and/or synthetic porous, microporous, mesoporous, or macroporous materials capable of receiving the sample fluid from the sample pad 150. The conjugate pad 110 may be made of material such as, for example, and without limitations, glass (e.g., glass fiber), cellulose, nitrocellulose, paper, silica, cotton, or synthetic material (e.g., polyester, polyethylene, polymers, rayon, nylon, etc.).

The conjugate pad 110 may contain a binding reagent (also referred to as antibody) that is capable of binding to the target analyte in the sample fluid. Depending on the type of the LFA, the binding reagent may be an antibody, an antigen, a protein, a nucleic acid, etc., that is capable of binding to the target analyte. For example, the conjugate pad 110 may contain the antibody to IgM and/or IgG conjugated with a label (or tag).

The binding reagent may be coupled to a label (also referred to as conjugate, detection conjugate, probe, or detector nanoparticle) which, in its natural state, is readily visible either to the naked eye, or with the aid of an optical filter. The label may be made of small particles (e.g., nanoparticles), such as, for example, and without limitations, metallic sols (e.g., colloidal gold or gold sol), dye sols, colored latex particles, carbon, etc. During the manufacture of the conjugate pad 110, the labeled binding reagent may be coated, impregnated, or otherwise applied or deposited on the conjugate pad 110 and then dried.

After the sample fluid flows from the sample pad 150 into the conjugate pad 110, the sample fluid may solubilize the labeled binding reagent. If the sample fluid contains the target analyte, the target analyte may bind with the labeled binding reagent and form an immunocomplex. The labeled binding reagents that do not bind with the target analyte (e.g., when the sample fluid does not include the target analyte or there is excess labeled binding reagent) flow downstream towards the membrane 115 by capillary action. The sample fluid and any other material in the flow path (e.g., unbound labeled binding reagents, wash fluid, etc.) are herein referred to as fluid material.

Depending on the type of test performed by the LFA device, the device may not include separate sample and conjugate pads in some embodiments and may only include the conjugate pad 110. Although the sample pad 150 is shown to go over the conjugate pad 110, in some embodiments, the conjugate pad 110 may go over the sample pad 150.

The membrane 115 may be fluidically connected (i.e., capable of receiving fluid, e.g., by capillary action) to the conjugate pad 110. A test line 101 may be embedded in the membrane 115. A control line 130 may also be embedded in the membrane 115. The membrane 115 may be made of a material such as, for example, and without limitations, cellulose, nitrocellulose, paper, silica, cotton, glass (e.g., glass fiber), or synthetic material (e.g., polyester, polyethylene, polymers, rayon, nylon, etc.) that allow the fluid material to flow downstream from the conjugate pad 110 into the membrane 115 and from the membrane 115 towards the wicking pad 120 by capillary action. Although the conjugate pad 110 is shown to go over the membrane 115, in some embodiments, the membrane 115 may go over the conjugate pad 110.

The test line 101 may be made of a porous material such as, for example, and without limitations, cellulose, nitrocellulose, paper, silica, cotton, glass (e.g., glass fiber), or synthetic material (e.g., polyester, polyethylene, polymers, rayon, nylon, etc.). In a sandwich assay format of the present embodiments, the test line 101 may contain the unlabeled binding reagents of several proteins of a target pathogen that are immobilized on the test line 101 and do not flow downstream when porous material of the test line is moistened (e.g., by the fluid material). Depending on a particular test made by the LFA device 100, the binding reagents immobilized on the test line may be the same or different than the binding reagent contained on the conjugate pad 110.

In the sandwich assay format, the binding reagents contained on the test line 101 may be immobilized antibodies that are capable of binding to the immunocomplex that is formed from the binding of the analyte with the labelled binding reagent on the conjugate pad 110. As the immunocomplex moves over the test line 101, the immunocomplex binds with the immobilized antibodies on the test line 101, resulting in a second immunocomplex that colors the test line 101. The intensity of the colored test line is correlated with the density of the analyte in the sample fluid. The second immunocomplex includes the analyte that is bound with the labelled binding reagent at one site and is bound with the immobilized binding agent at another site. When the sample fluid does not include the target analyte, no immunocomplex is formed on the conjugate pad 110 and no immunocomplex binds with the immobilized antibody on the test line 101. As a result, the test line 101 does not change color.

In a competitive assay format, the conjugate pad 110 may be similar to the conjugate pad of the sandwich assay format and may contain the labelled binding reagent to the target analyte (e.g., the binding reagent to the IgM and/or IgG). In the competitive assay format, the test line 101 may contain the immobilized analyte molecule (or a protein-analyte complex).

In the competitive assay format, if the sample liquid does not contain the analyte, the labeled antibody that is solubilized by the sample liquid may flow from the conjugate pad 110 into the test line 101 and may bind to the analyte at the test line 101, resulting in a colored test line 101 that indicates the lack of the target analyte in the sample liquid. If the target analyte is present in the sample liquid, the analyte may bind to the labeled antibodies on the conjugate pad 110 and may prevent the labeled antibody to bind to the analyte at the test line 101. As a result, the test line 101 may not change color, indicating the presence of the analyte in the sample fluid.

In the sandwich assay format, the control line 130 may contain immobilized antibodies that bind to the free labeled binding reagents resulting in a colored control line 130, which confirms that the test has operated correctly regardless of whether or not the target analyte has been present in the sample. For example, the control line 130 may contain immobilized antibodies that binds to the free labelled binding reagents to the IgM and/or IgG that flow over the control line.

In the competitive assay format, the control line 130 may contain immobilized analyte molecules (or protein-analyte complexes) that bind to the free labeled binding reagents resulting in a colored control line 130, which confirms that the test has operated correctly regardless of whether or not the target analyte has been present in the sample. For example, the control line 130 may contain immobilized IgM and/or IgG molecules that bind to the free labelled binding reagent to the IgM and/or IgG.

The fluid material that do not bind to the test line 101 or the control line 130 may continue to flow from the membrane 115 into the wicking pad 120. The wicking pad 120 may absorb the fluid material that are not taken up by the test line 101 and the control line 130 while maintaining the capillary flow from the membrane 115 into the wicking pad 120. The wicking pad 120 may be made of a porous material such as, for example, and without limitations, cellulose, nitrocellulose, paper, silica, cotton, glass (e.g., glass fiber), or synthetic material (e.g., polyester, polyethylene, polymers, rayon, nylon, etc.). Depending on the type of test performed by the LFA device, the device may not include a wicking pad 120. Although the wicking pad 120 is shown to go over the membrane 115, in some embodiments, the membrane 115 may go over the wicking pad 120.

The LFA device 100 may include a backing card 140 that is used to assemble different portions of the LFA device 100. The backing card, in some embodiments, may be a continuous piece that may go under the pads 150, 110, 115, and 120. In other embodiments, each pad may have a separate backing card. For example, during the manufacturing of the device, a roll or sheet of backing material may be used such that the width of the roll or the sheet is the same as (or is cut to be the same as) the length of the LFA cartridge (i.e., in the pictured orientation, from the left end of the sample pad 150 to the right end of the wicking pad 120). The membrane pad 115, the conjugate pad 110, the sample pad, 150, and the wicking pad 120 are then placed on the backing card with the proper overlaps (e.g., as shown in FIG. 1). The pads may, for example, be connected to the backing card with a two sided tape or glue. The pads and the attached backing card may then be cut into separate strips and each strip may be used to make a different LFA device.

Alternatively, each pad may be separately connected to a corresponding backing card. The pads with the corresponding backing cards may then be assembled over each other with the proper overlaps to make a LFA device. The LFA device 100 may include a housing. In FIG. 1, only a portion of the housing that includes the cartridge bed 170 is shown for simplicity.

Figure 3:
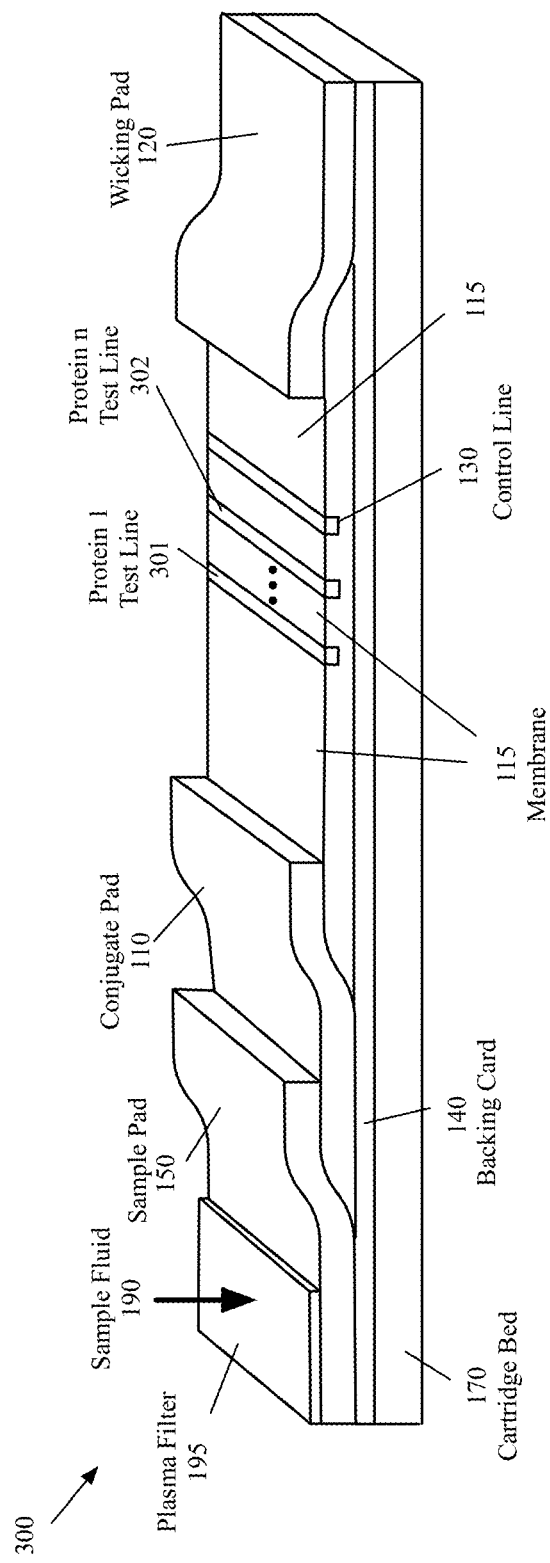
FIG. 3 is an upper front perspective view of an example of a portion of an LFA, where different proteins may be immobilized on different test lines next to each other, according to various embodiments of the present disclosure.

FIG. 3 is an upper front perspective view of an example of a portion of an LFA device 300, where different proteins may be immobilized on different test lines next to each other, according to various embodiments of the present disclosure. With reference to FIG. 3, the LFA device 300 may be configured to detect the presence of antibodies to a particular pathogen. As shown in the alternative embodiment of FIG. 3, different proteins may be immobilized on different test lines 301-302 next to each other. For example, the test line 301 may include protein 1 of the target pathogen and the test line 302 may include protein "n" of the target pathogen, with 0 or more additional test lines between the test line 301 and 302, one test line for each additional protein of the target pathogen.

In the embodiment of FIG. 3, it may be possible to identify which one of the proteins of the virus the immune response was generated against. However, the color intensity of these lines may be lower than that of the LFA device 100 of FIG. 1 where all proteins are mixed on one test line 101, which might be the desirable method when the identification of the individual responses to each protein is not of interest.

As another alternative, instead of having one test line for each protein, the LFA device of the present embodiments may combine two (or more) proteins per test line to reduce the number of consecutive test lines. For example, some of the LFA device of the present embodiments may include two or more test lines, with at least one test line having two or more proteins of the target pathogen immobilized on the test line. As another alternative, each test line may be split in two halves with a separation in between each half containing a different protein. As another alternative, each test line may be split into more than two portions with a separation in between each two adjacent portions containing a different protein. Any combination of the above arrangements may be used depending on the amount of available sample, the desired length and the flow characteristics of the membrane paper.

Figure 4:
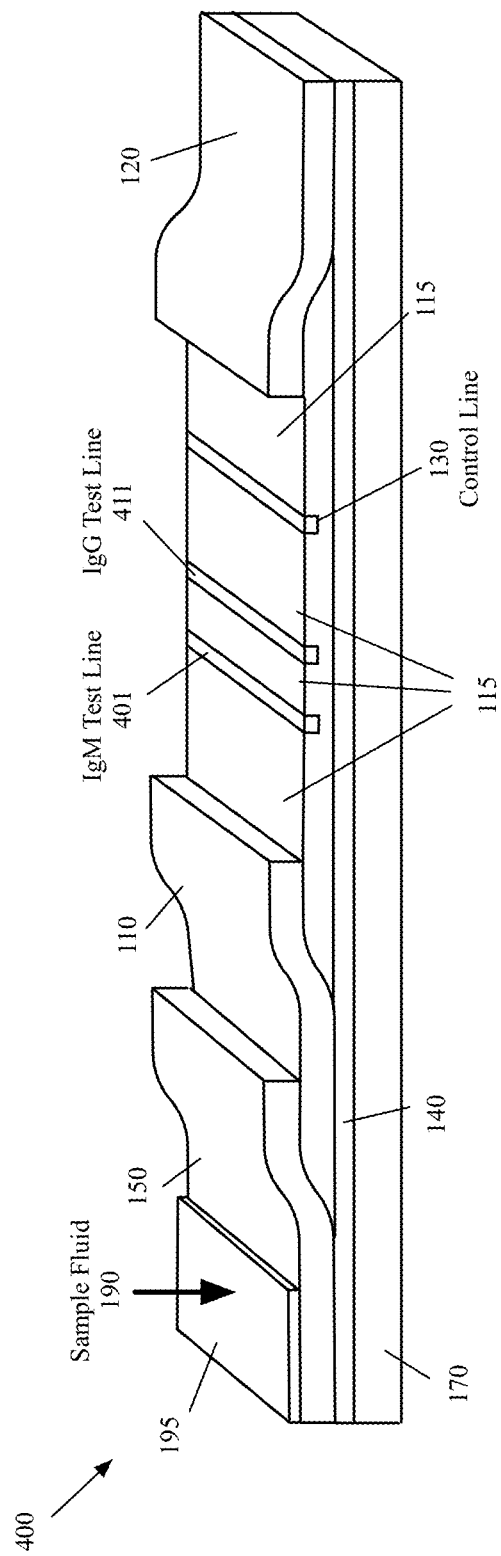
FIG. 4 is an upper front perspective view of an example of a portion of an LFA for detecting both IgM and IgG on two different test lines, where one test line contains the antibody to IgM and another test line contains the antibody to IgG, according to various embodiments of the present disclosure.

FIG. 4 is an upper front perspective view of an example of a portion of an LFA device 400 for detecting both IgM and IgG on two different test lines, where one test line contains the antibody to IgM and another test line contains the antibody to IgG, according to various embodiments of the present disclosure. With reference to FIG. 4, the LFA device 400 may be configured to detect the presence of antibodies to a particular pathogen. The conjugate pad 110 of the LFA device 400 may contain either all or some (i.e., a plurality of two or more) of the proteins of the target pathogen (e.g., and without limitations, a virus), each conjugated with a label.

If the sample 190 contains IgM or IgG antibodies that are specific to the target pathogen through any of the target pathogen's proteins, a binding may take place between those antibodies and the corresponding tagged pathogen's protein. The complex may then flow over the membrane 115 towards the test lines 401 and 411. The test line 401 may contain the binding reagent to IgM class resulting in the concentration of all the IgM molecules (e.g., a mix of the IgM molecules against any of the target pathogen's proteins generated by the immune system, which for the example of the SARS-CoV2 virus 200 of FIG. 2A may be any number of the proteins 205-225) that are specific to the pathogen. Similarly, the test line 411 may contain the binding reagent to the IgG class resulting in the concentration of all the IgG molecules (e.g., a mix of the IgG molecules against any of the target pathogen's proteins generated by the immune system, which for the example of SARS-CoV2 virus 200 of FIG. 2A may be any number of the proteins 205-225) that are specific to the virus.

The control line 130 of FIG. 4 may contain immobilized binding reagents to bind with the free labeled proteins of the target pathogen. Any free labeled proteins of the target pathogen that reaches the control line 130 may be immobilized by the binding reagents, resulting in a change of color of the test line 130.

The LFAs of the present embodiments provide the technical advantage of increasing the sensitivity of the test by mobilizing multiple proteins of a target pathogen on one or more test lines. The multiple proteins may capture any of the IgM or IgG responses regardless of which protein of the target pathogen the response has been generated for. In contrast, the prior art LFAs, as described below, may produce a false negative contributing to the low sensitivity of the test.

Figure 5:
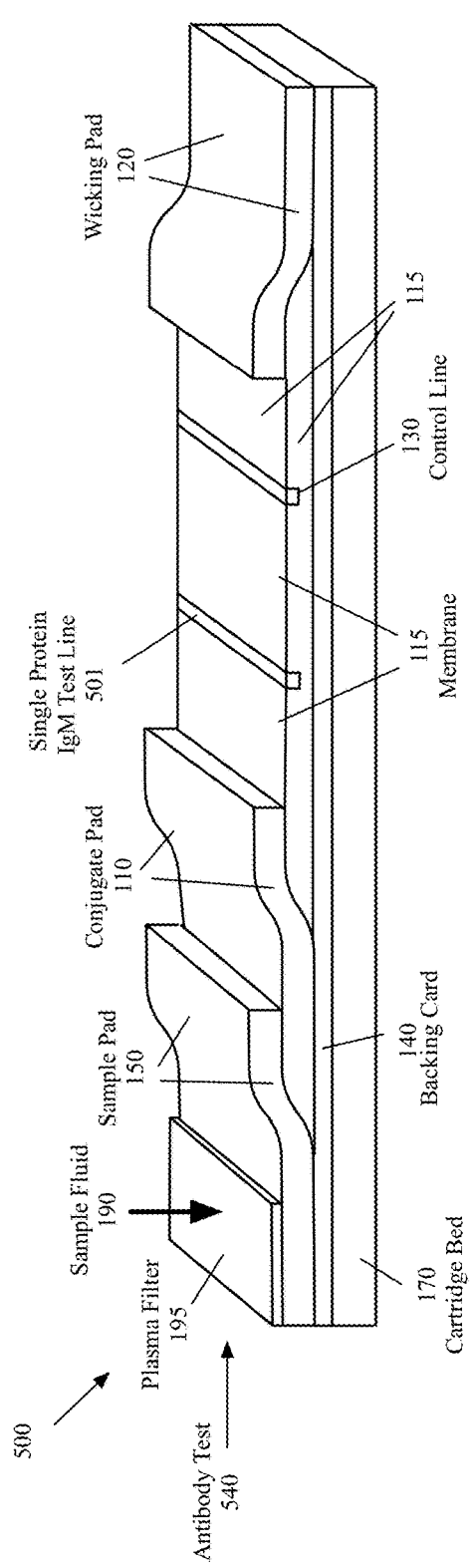
FIG. 5 is an upper front perspective view of an example of a portion of a conventional LFA for an IgM antibody test for SARS-CoV2 virus, according to prior art.

FIG. 5 is an upper front perspective view of an example of a portion of a conventional LFA device 500 for an IgM antibody test 540 for SARS-CoV2 virus, according to prior art. The LFA 500 is currently offered by several manufacturers of LFA devices. A drop of blood 190, for example, from a finger prick, is applied to the input sample section (e.g., the plasma filter) of the LFA device followed by the addition of a small amount of buffer solution. The sample first flows through the plasma filter 195 that separates the plasma from the whole blood and flows from the sample pad 150 to the conjugate pad 110.

The conjugate pad 110 may contain antibodies against the general IgM class that have been conjugated with a tag (e.g., gold nanoparticles). As the sample flows through the conjugate pad 110, any IgM in the sample may be attached to this tagged IgM antibody and the combined complex may flow through to the membrane 115 and towards the test line 501.

A concentrated amount of the N protein of the SARS-CoV2 virus (recombinant N protein) is immobilized on the test line 501. As the combined complex passes through the test line, any IgM that is specific to the SARS-CoV2 virus may get attached to the test line 501.

Since these IgM molecules are also attached to the anti-IgM antibody with gold particles, a concentration of gold particles may be formed at the test line 501 and the test line may show a red colored band indicative of a positive test. The rest of the fluid which contains leftover anti-IgM antibodies conjugated with gold particles may flow through the membrane 115 and may be stopped at the control line 130 which contains immobilized particles that attach to those anti-IgM antibodies and form a concentration of the gold particles turning the control line to red color.

If there are no IgM molecules that are specific to the N protein of the SARS-CoV2 virus present in the sample then the test line 115 may show no color change indicating a negative test but the control line 130 may show a red line. The control line 130 always shows the red line regardless of the test being positive or negative which is an indication that the test took place properly. If the control line 130 does not change color, the test is invalid. The same test may be performed for the IgG antibody in the same manner explained above with the difference that the conjugate pad 110 contains antibodies against IgG that have been conjugated with a tag.

It is also possible to switch the role of the protein on the test line 501 and the antibody against either IgM or IgG on the conjugate pad 110. In that case, the conjugate pad may contain the protein (e.g., the N-protein 225 of SARS-CoV2 virus 200 of FIG. 2A) conjugated with the tag and the test line 501 may contain the antibody against IgM or IgG.

Figure 6:
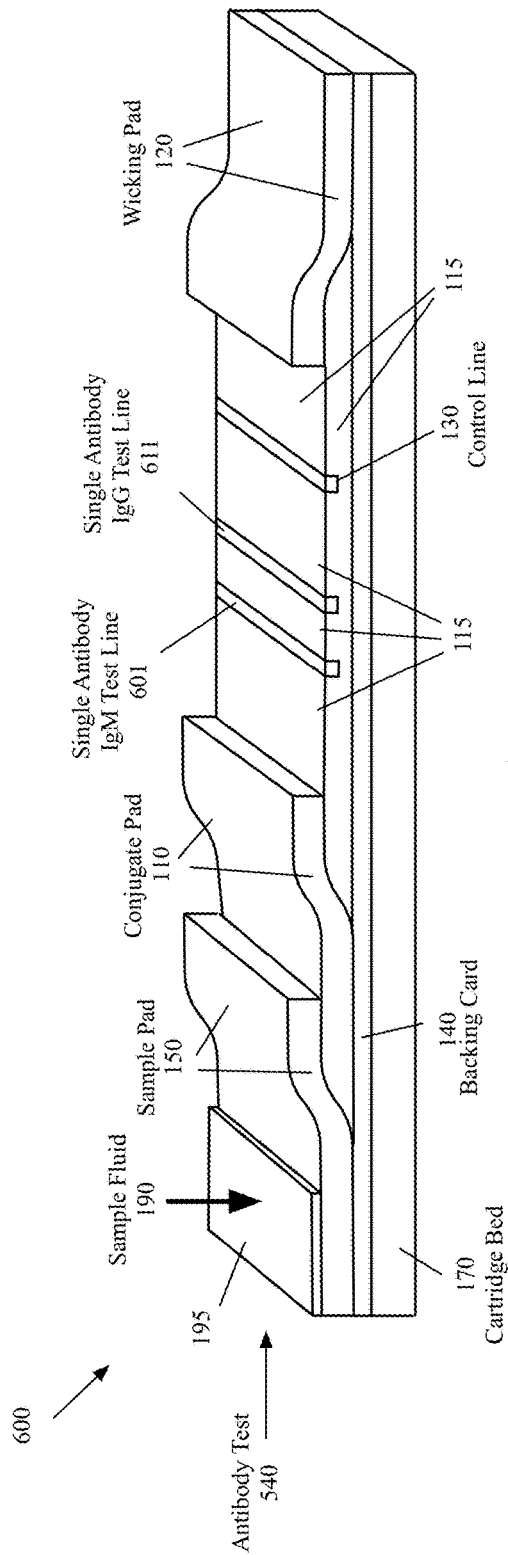
FIG. 6 is an upper front perspective view of an example of a portion of a conventional LFA, where both the IgM and IgG are detected on the same LFA strip on two different test lines, according to prior art.

FIG. 6 is an upper front perspective view of an example of a portion of a conventional LFA device 600, where both the IgM and IgG are detected on the same LFA strip on two different test lines, according to prior art. With reference to FIG. 6, the conjugate pad 110 may contain the protein (e.g., the N-protein 225 of SARS-CoV2 virus 200 of FIG. 2A) conjugated with a tag. The first test line 601 may contains the antibody to IgM and the second test line 611 may contain the antibody to IgG. If the sample 190 contains any IgM or IgG that are specific to the SARS-CoV2 virus and against the N-protein of the virus, they bind to the conjugated N-protein on the conjugate pad 110. This complex may then flow on the membrane 115 where the combined molecules that have the IgM specific to the virus may get concentrated at the first test line 601 and the combined molecules that have the IgG specific to the virus may get concentrated at the second test line 611.

The IgM/IgG tests provided by the LFA devices 500 and 600, which are referred to as serology tests or antibody response tests in the market, generally show a very high specificity even up to 100% meaning that there are very small number or even zero false positives but the false negatives are high (low sensitivity) for IgM at the early stage of the infection.

Figure 7:
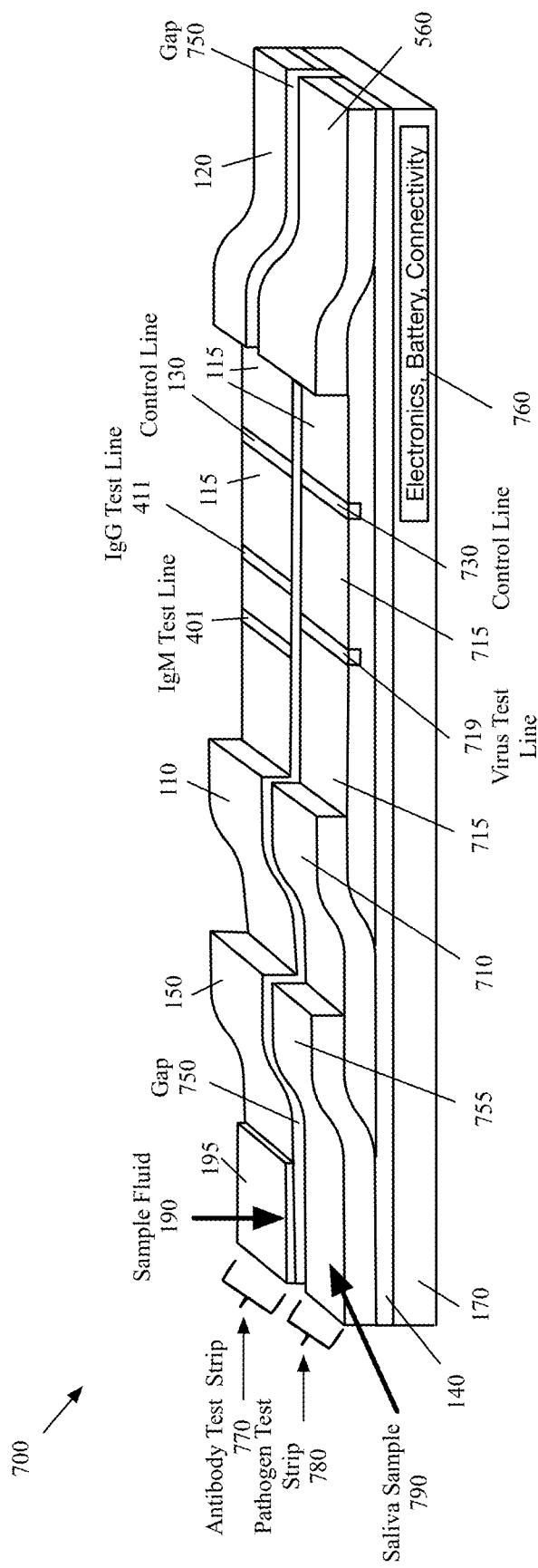
FIG. 7 is an upper front perspective view of an example of a portion of a dual strip LFA device for testing the antibodies against a target pathogen using a blood sample as well as detecting the presence of the pathogen itself in a saliva sample, according to various embodiments of the present disclosure.

II. LFA Device with Dual Strips for Detecting the Presence of a Virus Using a Saliva Sample and Testing the IgM and IgG Response Using a Blood Sample FIG. 7 is an upper front perspective view of an example of a portion of a dual strip LFA device 700 for testing the antibodies against a target pathogen using a blood sample as well as detecting the presence of the pathogen itself in a saliva sample, according to various embodiments of the present disclosure. With reference to FIG. 7, the dual strip LFA device 700 may include a test strip 770 for testing the antibodies against a target pathogen and a test strip 780 for testing the presence of the target pathogen itself. The test strips 770 and 780 may be separated by a gap 750 that may prevent any fluids from flowing from one test strip 770-780 into the other.

The dual strip LFA device 700 may include a cartridge (only the cartridge's bed 170 is shown for clarity) that encompasses both of the test strips 770 and 780. Each of the test strips 770 and 780 may include separate sample input ports (not shown), separate sample pads 150 and 755, separate membranes 115 and 715, separate test lines 401-411 and 719, separate control lines 130 and 730, and separate wicking pads 120 and 720.

The test strip 770, in some embodiments, may have similar components as, and may function similar to, the LFA device 400 of FIG. 4. The test strip 770, in some embodiments, may have similar components as, and may function similar to, the LFA device 300 of FIG. 3. Yet, in some embodiments, the test strip 770 may have similar components as, and may function similar to, the LFA device 100 of FIG. 1.

With continued reference to FIG. 7, the test strip 770 may be used for testing the IgM and IgG response using a blood sample 190 from a finger prick and the test strip 770 may be used for detecting the presence of the target pathogen (e.g., the presence of the SARS-CoV2 virus) using a saliva sample 790.

The pathogen detection strip 780 may function as follow. Either the saliva sample 790 or a mix of the saliva sample 790 with a buffer solution may be placed on the sample pad 755. The sample may flow to the conjugate pad 710, which may contain the binding reagent to one of the proteins of the target pathogen. For example, and without limitations, the conjugate pad 710 may contain the binding reagent to the N protein 225 of the SARS-CoV2 virus 200 of FIG. 2A that is conjugated with a tag.

After a binding step on the conjugate pad 710, the solution may flow over the membrane 715 and may reach the test line 719 which may contain the binding reagent to a different protein of the target pathogen or a binding reagent to the same protein different from the binding reagent used on the conjugate pad. For example, the test line 719 may contain the binding reagent to the S protein 205 of the SARS-CoV2 virus 200. The test line 719 may contain the binding reagent to the N protein 205 of the SARS-CoV2 virus 200 to bind to another N protein 205 on the same SARS-CoV2 virus 200 in the event that not all N proteins of the pathogen are bound to the binding reagent of the conjugate pad. Alternatively, the test line 719 may contain another type of binding reagent (that is different than the binding reagent on the conjugate pad) to the N protein 205 of the SARS-CoV2 virus 200 to bind to the N protein 205 on the same SARS-CoV2 virus 200.

If the sample 790 contains the pathogen, the pathogens bind with the conjugated binding reagents to the first protein (e.g., the N protein 225 of SARS-CoV2 virus 200), flow towards the test line 719, and are stopped at the test line 719 by binding to the binding reagent against another one of the virus's proteins (e.g., the S protein 205 of the SARS-CoV2 virus 200) or against a binding reagent to the same protein different from the binding reagent used on the conjugate pad. The concentration of the pathogen, and hence the tag, may result in a color change of the test line 719. The intensity of the color change may be correlated with the concentration of the target pathogen.

The test line 730 may contain the immobilized antibodies (or binding reagents) to bind with the free binding reagents of the proteins of the target pathogen. Any free binding reagents of the proteins of the target pathogen that flows over the control line 730 may bind to the immobilized binding reagents, resulting in a colored test line 730.

As shown by 760, the dual test architecture of FIG. 7 may include a location determination component, such as a Global Positioning System (GPS) receiver, a microcontroller, one or more transceivers such as Bluetooth, Wi-Fi, or NFC transceivers, along with a battery, all integrated in one dual strip test cartridge 700.

The dual test architecture of FIG. 7 may include a sensor to read the test results. For example, in the embodiments that the label includes gold particles, the sensor may be a light sensor (or photo sensor) that may read the intensity of light reflected from the test lines 401, 411, and/or 729, and/or the light reflected from the control lines 130 and 730. The reading may be a quantitative reading. The reading, in some embodiments, may be converted to a positive or negative result by the microcontroller. The sensor, in some embodiments, may be integrated with the LFA device 700. For example, the sensor may be installed on the cartridge of the LFA device over the test lines and control lines. The sensor, in some embodiments, may be part of an external device. For example, and without limitations, the sensor may be a photo sensor integrated in an external electronic device, such as a smartphone.

The microcontroller may receive the test results from the sensor and may receive location of the LFA device from the GPS reviser. The microcontroller may transmit, through the transceiver(s), the location of the LFA device where a test is performed and test results to one or more external electronic devices.

A software platform on the external electronic devices may communicate with the microcontroller, either directly through the test cartridge, or through a smart phone paired with the test cartridge. The software platform may receive the location of the LFA device and the test results from the microcontroller, and may keep track of all important aspects of the test including the test location and the test results.

The saliva test strip may require higher sensitivity than offered by conventional LFA devices in which case the next generation LFA technology with embedded flow described in U.S. patent application Ser. No. 16/698,788, entitled Lateral Flow Assay with Controlled Conjugate and Controlled Flow Time, and filed on Nov. 27, 2019, issued as U.S. Pat. No. 10,739,297, may be employed to achieve the desired sensitivity in detecting the target pathogen.

As an alternative method for detecting the presence of the virus in saliva, the saliva sample 790 may be mixed with a detergent solution which lyses the saliva cells and releases the proteins of the virus, in particular the S protein of the virus. Two different antibodies to the S protein may then be used with the LFA device to form a sandwich assay. The resulting LFA device may require higher sensitivity than what is offered by conventional LFA devices in which case the next generation LFA technology with embedded flow described in the above-mentioned U.S. Pat. No. 10,739,297 may be employed to achieve the desired sensitivity in detecting the target pathogen. The time required for the detergent to lyse the cells is generally longer than the binding time offered by the conjugate pad in conventional LFA devices not allowing for this step to be integrated in the LFA device and requiring an external step of mixing the saliva sample with the appropriate detergent solution. One of the advantages offered by the next generation LFA technology described in the above-mentioned U.S. Pat. No. 10,739,297 is the ability to program the binding time of the conjugate pad which enables the integration of the detergent step into the LFA device itself.

III. Blood Drawing and Mixing Module

The lateral flow test devices that use blood as the input sample particularly those that are intended for home use using the fingertip blood, have to mix the blood sample with a buffer or reagent solution prior to placing the sample on the input sample pad of the device. In some commercial test kits for home or point of care use, a lancet may be used to prick a person's fingertip and a drop of blood may be squeezed on the sample input opening of the device followed by dropping a few drops of the buffer or reagent solution from a solution bottle provided with the kit. This process is not straightforward and often causes the blood to spill on the plastic cartridge body of the test kit and not make it to the sample pad. The manual dropping of the buffer solution is also an extra error-prone step which adds to the complication of the process.

Figure 8:
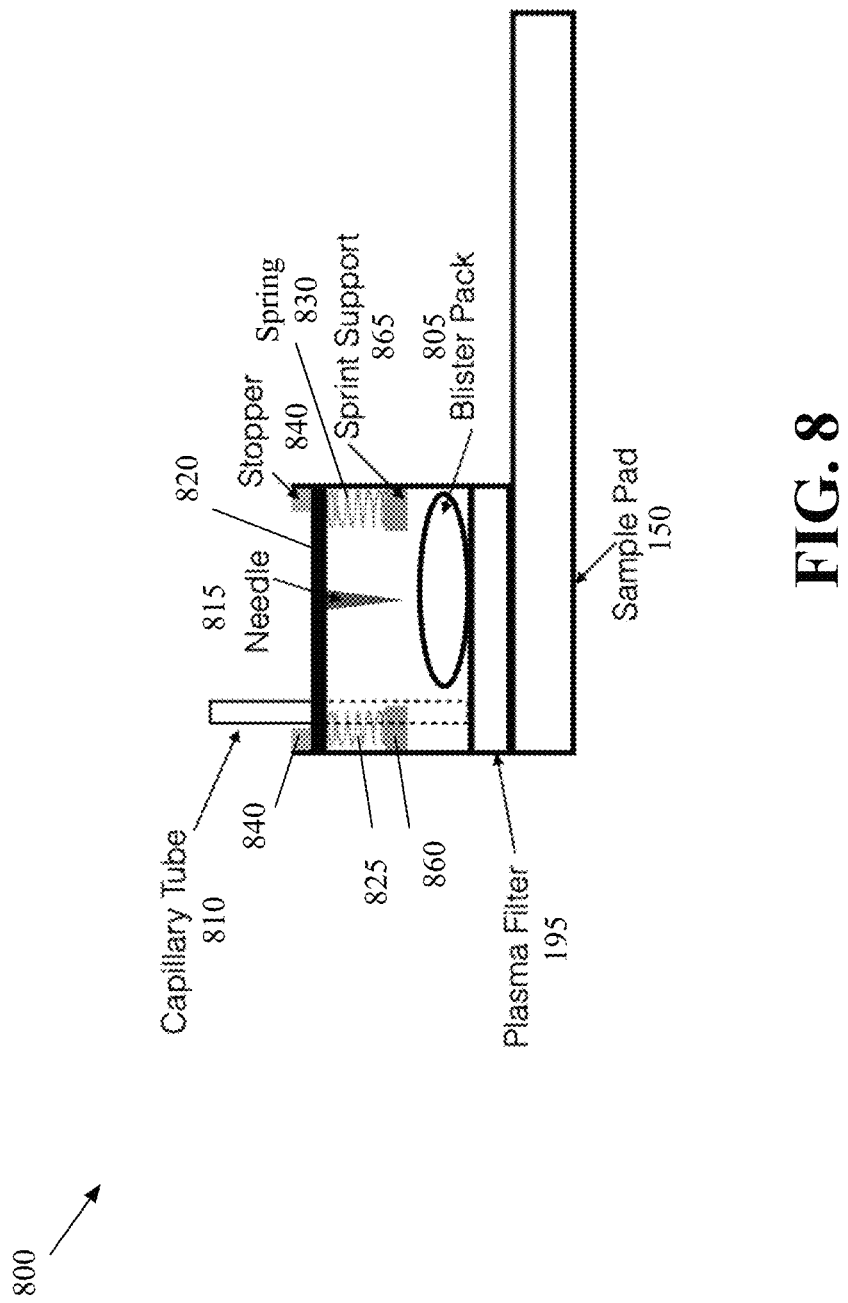
FIG. 8 is a front view of a blood drawing and mixing module, according to various embodiments of the present disclosure.

The system shown in FIG. 8 automates these steps providing a simple-to-use test kit with minimal instructions. FIG. 8 is a front view of a blood drawing and mixing mechanism 800, according to various embodiments of the present disclosure.

With reference to FIG. 8, a blister pack 805 containing the buffer or reagent solution (or the detergent solution described above with reference to FIG. 7), a capillary tube 810, a needle 815 attached to a plate 820, four springs 825-830 (only two springs are showing in the front view of FIG. 8), four stoppers 840 (only two stoppers are showing in the front view of FIG. 8), and four spring supports 860-865 (only two spring supports are showing in the front view of FIG. 8) may be integrated in a single module that directly sits on top of the sample pad 150, or the plasma filter pad 195 (if one is present) of the LFA device. The blood drawing and mixing module 800 may be part of the enclosure of the test cartridge, which, for example, may be made of plastic.

The capillary tube 810 and the blister pack 805 directly touch the surface of the plasma filter 195. The user may prick his/her finger with a conventional lancet and may hold the capillary tube against the drop of blood formed on the fingertip. The capillary action draws the blood in and guides it to the plasma filter pad 195. Since the capillary tube 810 directly touches and pushes against the surface of the plasma filter's 195 paper, the capillary action continues to draw the blood sample into the plasma filter 195. The user may then push the needle plate 820 down. The needle 815 may punch the top and bottom of the blister pack 805 and may cause the buffer or reagent solution to spill over the plasma filter's 195 paper. Again, the capillary action of the filter paper helps pulling the solution in. The buffer or reagent solution are mixed and go through the plasma filter 195 and reach the sample pad 150, which may absorb and move the filtered solution. The stoppers 840 may hold the needle plate 820 from moving further up by the springs 830.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure.

What is claimed is:

1. A lateral flow assay device, comprising:
a test strip configured to receive a sample fluid and detect a presence of antibodies to a target pathogen, each antibody specific to one of a plurality of proteins of the target pathogen, each antibody belonging to one of a plurality of classes of antibodies, the test strip comprising:
a conjugate pad,
wherein the conjugate pad is configured to receive a quantity of fluid after a start of a test and move the fluid by capillary action, and
wherein the conjugate pad is configured to contain a plurality of three or more different proteins of the target pathogen conjugated with a label, and
a membrane fluidly connected to the conjugate pad,
wherein the membrane is configured to move the fluid by capillary action,
wherein the membrane comprises a first test line comprising an immobilized binding reagent to a first class of antibodies, and
wherein the membrane comprises a second test line comprising immobilized binding reagents to a second class of antibodies, wherein the target pathogen is SARS-CoV-2 virus.

2. The lateral flow assay device of claim 1, wherein the membrane comprises a control line comprising immobilized binding reagents configured to bind to the plurality of proteins of the target pathogen conjugated with the label.

3. The lateral flow assay device of claim 1, wherein the test strip is a first test strip, wherein the sample fluid is a first sample fluid, the lateral flow assay device further comprising:
a second test strip configured to receive a second sample fluid and detect a presence of the target pathogen, the second test strip comprising:
a conjugate pad,
wherein the conjugate pad of the second test strip is configured to receive a quantity of the second sample fluid after the start of the test and move the second sample fluid by capillary action, and
wherein the conjugate pad of the second test strip is configured to contain binding reagents to a first protein of the plurality of the proteins of the target pathogen, the binding reagent conjugated with a label, and a membrane fluidly connected to the conjugate pad of the second test strip,
wherein the membrane of the second test strip is configured to move the second sample fluid by capillary action,
wherein the membrane of the second test strip comprises a test line comprising immobilized binding reagents to a second protein of the plurality of proteins of the target pathogen, wherein the first and second proteins are different proteins.

4. The lateral flow assay device of claim 3 further comprising a cartridge encompassing the first and second test strips.

5. The lateral flow assay device of claim 3 further comprising a gap between the first and second test strips, the gap configured to prevent any fluid flowing from one test strip to the other test strip.

6. The lateral flow assay device of claim 3, wherein the second sample fluid comprises one of a saliva sample and a mix of a saliva sample and a buffer solution.

7. The lateral flow assay device of claim 3, wherein the second sample fluid comprises a saliva sample mixed with a detergent solution that is configured to lyse saliva cells in the saliva sample and release the proteins of the target pathogen.

8. The lateral flow assay device of claim 3, wherein the membrane of the second test strip comprises a control line comprising immobilized binding reagents configured to bind to the binding reagents to the first protein of the plurality of the proteins of the target pathogen conjugated with the label.

9. The lateral flow assay device of claim 8 further comprising:
a Global Positioning System (GPS) receiver;
a microcontroller;
one or more transceivers;
one or more light sensors configured to:
read an intensity of light reflected from at least one of the test lines of the first strip, the test line of the second strip, the control line of the second strip, and a control line of the first strip; and
provide the results to the microcontroller;
wherein the microcontroller is configured to:
keep track of a location of the lateral flow assay device through the GPS receiver; and
transmit the location of the lateral flow assay device and a result of a test performed by the lateral flow assay device through the transceivers to one or more electronic devices external to the lateral flow assay device.

10. The lateral flow assay device of claim 1, wherein the sample fluid is a blood sample.

11. The lateral flow assay device of claim 1, wherein the first and second classes of the antibodies are one of immunoglobulin A (IgA), immunoglobulin D (IgD), immunoglobulin E (IgE), immunoglobulin G (IgG), and immunoglobulin M (IgM), and wherein the first class of antibodies is different than the second class of antibodies.

12. The lateral flow assay device of claim 1, wherein the label is a detector comprising at least one of metallic sols comprising colloidal gold, dye sols, colored latex particles, and carbon.

13. The lateral flow assay device of claim 1 further comprising a wicking pad configured to maintain a capillary flow from the membrane into the wicking pad.

14. The lateral flow assay device of claim 1, wherein the target pathogen is one of a bacterium, a virus, a protozoan, a prion, a viroid, and fungus.

15. The lateral flow assay device of claim 1 further comprising a sample pad configured to receive the sample fluid and transfer the sample fluid by capillary action to the conjugate pad.

16. The lateral flow assay device of claim 1 further comprising a plasma filter configured to receive the sample fluid and transfer the sample fluid to one of the conjugate pad and a sample pad of the lateral flow assay device.

17. The lateral flow assay device of claim 1 further comprising a blood drawing and mixing mechanism, the blood drawing mechanism comprising:
a capillary tube, the capillary tube configured to receive one or more drops of blood and transfer the one or more drops of blood to a capillary pad of the lateral flow assay device, the capillary pad comprising one of a plasma filter and a sample pad.

18. The lateral flow assay device of claim 17, the blood drawing and mixing mechanism further comprising:
a blister pack containing a quantity of fluid, the blister pack configured to contact the capillary pad;
a needle plate; and
a needle connected to the needle plate and pointing towards the blister pack;
wherein the needle plate is configured to receive a force and move the needle to pierce the blister pack, releasing the fluid contained in the blister pad on the capillary pad.

19. The lateral flow assay device of claim 18, the blood drawing and mixing mechanism further comprising:
a plurality of springs configured to move the needle plate away from the blister pack when the force is removed from the needle plate; and
a plurality of stoppers configured to limit a distance the needle plate moves away from the blister pack by the plurality of springs.

20. The lateral flow assay device of claim 18, wherein the fluid contained in the blister pack comprises one of a buffer and a reagent solution.

* * * * *